(12) United States Patent
Colburn et al.

(10) Patent No.: US 6,213,980 B1
(45) Date of Patent: Apr. 10, 2001

(54) FILL FACILITATING UNIT DOSE INJECTION CARTRIDGE AND FILLING METHOD

(75) Inventors: Theodore J. Colburn; Sabrena A. Wright, both of King County, WA (US)

(73) Assignee: PATH, Seattle, WA (US)

( * ) Notice: Subject to any disclaimer, the term of this patent is extended or adjusted under 35 U.S.C. 154(b) by 0 days.

(21) Appl. No.: 09/426,719

(22) Filed: Oct. 26, 1999

(51) Int. Cl.[7] .................................................. A61M 5/178
(52) U.S. Cl. ............................................................. 604/183
(58) Field of Search ................................ 604/68, 72, 140, 604/141, 143, 147, 152, 154, 157, 257, 261, 228; 222/340, 372, 341, 320, 575

(56) References Cited

U.S. PATENT DOCUMENTS 4,655,747 * 4/1987 Allen, Jr. ............................... 604/89
5,938,637 * 8/1999 Austin et al. ............................ 604/72

\* cited by examiner

Primary Examiner—Manuel Mendez
(74) Attorney, Agent, or Firm—Banner & Witcoff, Ltd.

(57) ABSTRACT

A unit dose injection cartridge (e.g., needleless injection cartridge) includes an elongated chamber, a sealable discharge outlet (e.g., nozzle orifice) and a piston seal slidable within the chamber from a proximal end region to a distal end of the chamber. The piston seal is movably securable at a first position within the proximal end region, wherein the chamber is fillable with medicament by way of a passageway extending past the piston seal from a proximal side to a distal side thereof. During filling, air is allowed to escape from the chamber through the same passageway used for filling, or a second similarly arranged adjacent passageway. Once a unit dose of medicament is metered into the chamber, the piston seal may be moved slightly distally to a second position within the proximal end region, whereby the chamber is sealed-off from the passageway by the piston seal. During this movement of the piston seal, and before the chamber is sealed-off, any air remaining in the chamber is allowed to escape through the passageway (or second passageway), avoiding the need for leakage of air and/or medicament through the orifice of the discharge nozzle. The passageway(s) may be provided between the plunger and an adjacent laterally recessed chamber wall portion, or alternatively as discrete passageways through the chamber-forming wall structure.

14 Claims, 4 Drawing Sheets

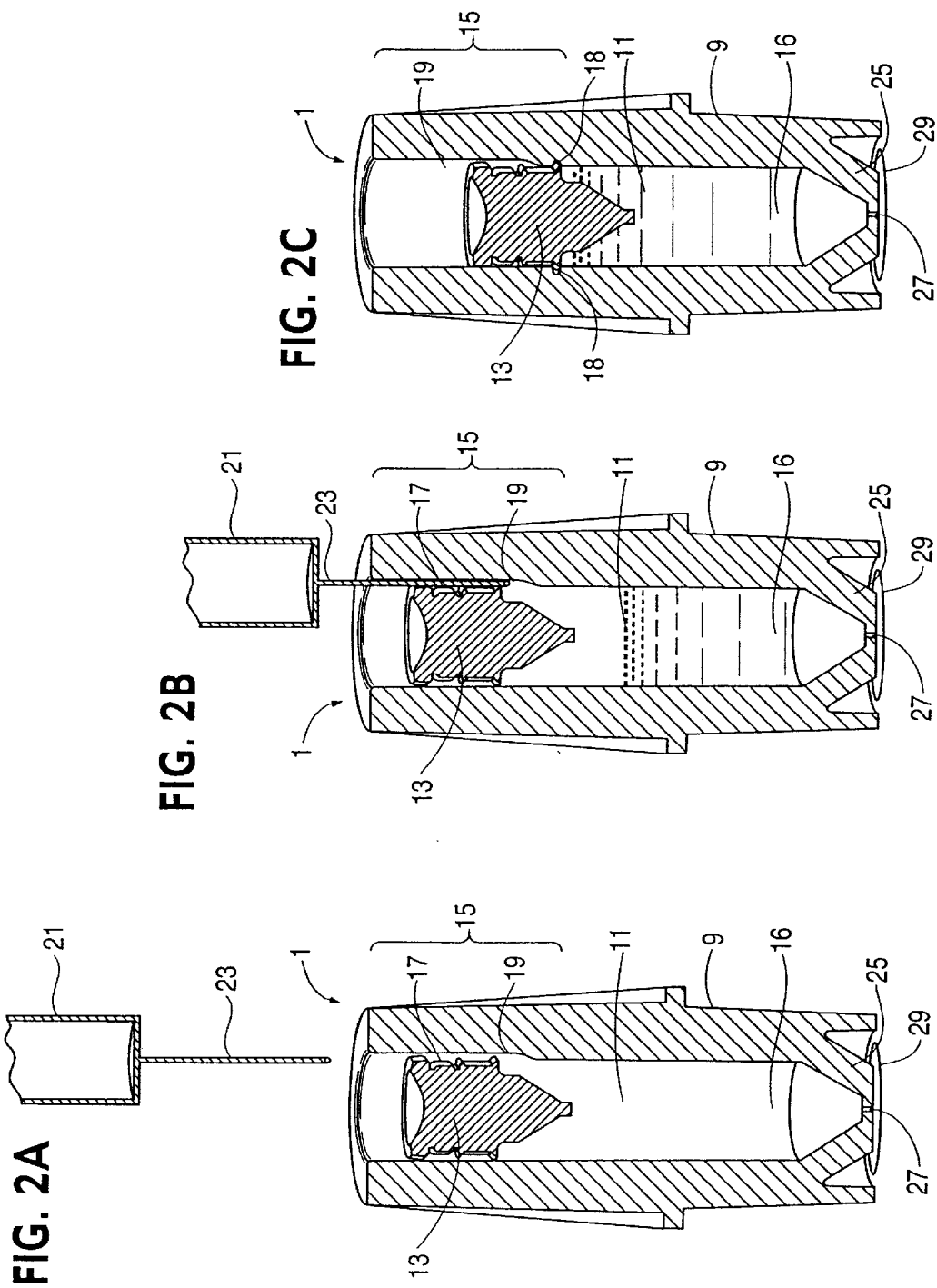

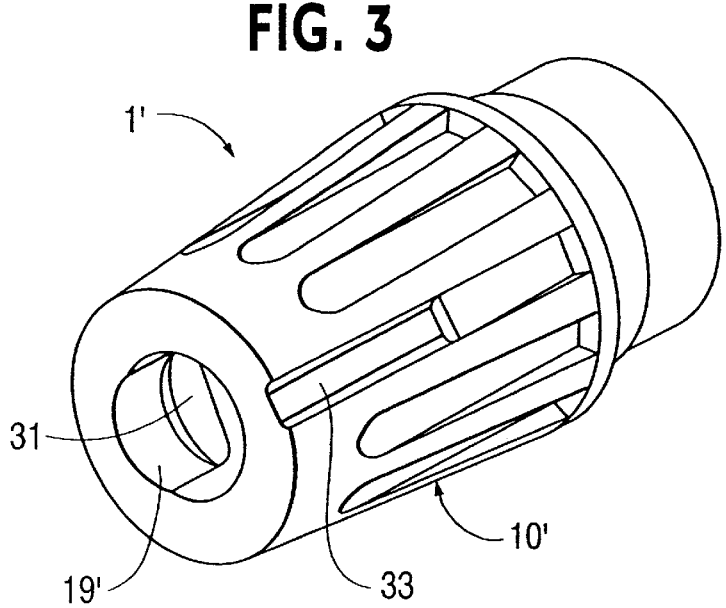
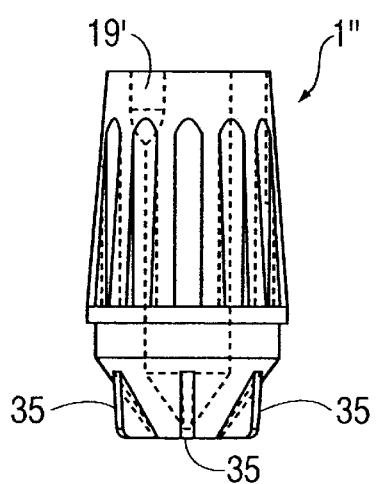
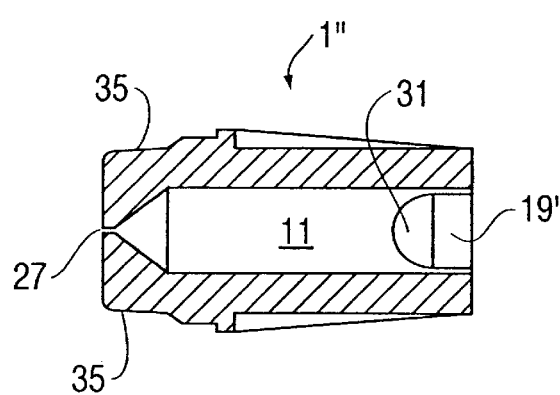
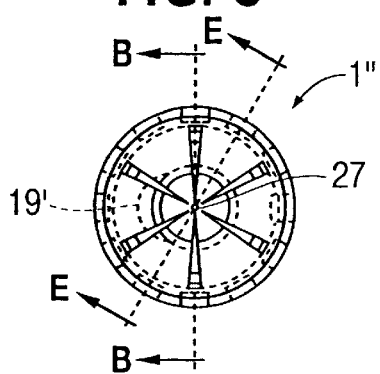
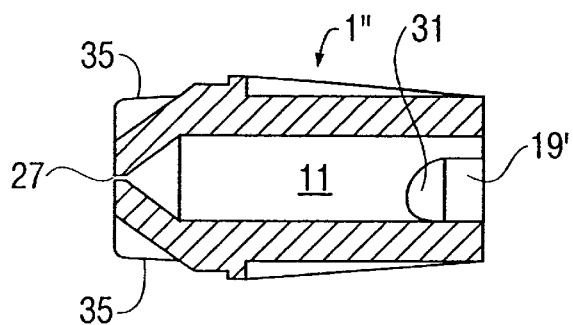

FILL FACILITATING UNIT DOSE INJECTION CARTRIDGE AND FILLING METHOD

FEDERALLY SPONSORED RESEARCH AND DEVELOPMENT

This invention was made in part with government support under Cooperative Agreement No. DPE-5968-A-00-0025-00 awarded by the Agency for International Development. The U.S. Government has certain rights in this invention.

BACKGROUND OF THE INVENTION

The present invention relates to injection cartridges and methods for filling the same with medicament. More specifically, the invention relates to injection cartridges or medicine delivery units for needleless hypodermic (subcutaneous) injectors, i.e., devices for delivering into a body a dose of liquid medicament by way of a fine high pressure liquid stream which penetrates the skin, and methods for filling the cartridges with medicament.

For years, health workers have administered medicine to patients using syringes and needles. (It is to be understood that "medicine" and "medicament" as used herein refers generally to any type of liquid medicament or vaccine.) However, the use of syringes and needles puts health workers and patients at risk of infection through inadvertent needle-sticks or equipment misuse. In addition, syringes and needles are difficult to disinfect or sterilize, and the use of improperly sterilized syringes and needles greatly increases the risk of blood-borne disease transmission among injection recipients. Still further, syringes and needles can cause a high level of anxiety in certain patients, and reuse of dull needles can cause extreme discomfort to the injection recipient.

Disposable syringes and needles have been used to alleviate the risk of disease transmission. However, these disposable units create hazardous waste and waste disposal problems. Inadvertent painful needle sticks and consequent spread of disease and infection may result from the handling of such medical waste. In addition, particularly in some areas of the world where disposable syringes and needles often do not reach the users in adequate quantities, the disposable units may be used more than once, contrary to their intended purpose. A further drawback to disposable needles and syringes is the high costs when the units are provided for widespread use.

Several types of needleless injectors have been developed to avoid some of the drawbacks of syringes and needles. Mass-campaign jet injectors, such as the PEDOJET™, have been used to provide fast and efficient needleless injections. However, these units are very difficult to clean or sterilize upon contamination. In addition, the mass-campaign injectors utilize a complex fluid path with dead space therein, such that a substantial amount of residual medicine is retained in the fluid path. When changing from one injectant to another, the residual fluid must be cleared to prevent unacceptable mixing of medicines. This clearing process wastes a relatively large amount of medicine before the injector is ready to inject another patient. Low-workload jet injectors, such as the VITAJET™ or the SICIM™ HYPODERMIC INJECTOR JET 2000, have also been used to provide needleless injections. These low-workload injectors also utilize a complex fluid path that retains residual medicine. Accordingly, the units are difficult to sterilize, and medicine is wasted through purging when changing between medicines to be administered.

Commonly assigned U.S. patent application Ser. No. 08/483,192, filed Jun. 7, 1995, now U.S. Pat. No. 5,746,714 (hereby incorporated by reference in its entirety), discloses an air-powered needleless hypodermic injector (hereinafter "APNHI") representing a significant improvement over previous designs in several respects. In particular, the injector includes a reusable (primarily stainless steel) medicine delivery unit. The delivery unit mounts in the front end of a main injector housing and is easily removed from the main injector housing for cleaning and/or sterilization, without the need for disassembly of the delivery unit.

A medicine chamber of the APNHI medicine delivery unit receives medicine from a medicine filling mechanism (including a medicine vial) through a unique side-loading fill port. A discharge piston is slidably mounted in the chamber and has a rear rod extension which engages with an air piston driven by a relatively low-pressure air source. During an injection, the air piston drives the discharge piston forward to force medicine in the chamber through an injection nozzle located at the distal end of the chamber, to form a high pressure injection stream. The design provides a simple, removable fluid path with essentially no dead space, and thereby allows medicines to be changed without purging waste. The provision of a side-loading fill port avoids cumbersome arrangements for filling the medicine delivery chamber through the front injection orifice, and the associated increased possibility of surface contamination, as exists in many other devices. In addition, since the side-loading fill port is located very close to the piston head when the piston is in its retracted position, the fill port is closed at the beginning of the piston's discharge stroke. Such positioning of the fill port eliminates the requirement (present in the rear-loading arrangements of other devices) of check-valves to prevent medicine from flowing out of the fill port during the discharge stroke. Such check valves increase costs and are subject to malfunction and leakage due to their repeated exposures to the extremely high injection pressures (e.g., 3000 psi) generated within the chamber.

In certain settings, such as mass immunization campaigns conducted away from health care facilities, it may be inconvenient or impractical to frequently perform cleanings and sterilization of injector components, e.g., the medicine delivery unit of the APNHI. In such settings, it would be highly desirable to be able to employ a low cost disposable medicine delivery unit that would reduce the need for equipment sterilizations.

Copending U.S. application Ser. No. 08/819,563, filed Mar. 14, 1997 (hereby incorporated by reference in its entirety) discloses a single use needleless medicine delivery unit formed of medical grade or commodity polymer. Similar to the medicine delivery unit of U.S. Pat. No. 5,746,714, the delivery unit employs a side-loading fill port for filling the delivery unit at the time of use, through a medicine vial and distributor forming part of the injector. Single use is ensured by the provision of means for positively disabling the medicine delivery unit after a single use, e.g., by retaining the plunger at the end of its injection stroke within a reduced diameter portion of the chamber and/or destroying the injection orifice with a protrusion at the distal end of the slidable piston seal.

The side-load port arrangements described in the '714 patent and application Ser. No. 08/819,563 have substantial advantages over previous known arrangements. However, like known rear-fill methods/arrangements, in order to completely fill the chamber of the delivery unit (leaving no air space) it is necessary to purge air from the chamber. This is typically done by forcing medicament into the chamber under pressure to the point where leakage (dribbling) from the unobstructed discharge outlet (nozzle orifice) occurs.

For certain applications, rather than filling the medicine deliver unit (injection cartridge) at or just prior to the time of injection, it is preferable to utilize pre-filled injection cartridges. This permits simplification of the injection apparatus and procedure, because the means and steps for delivery of medicine to the cartridge can be dispensed with. While transferring liquids into vials is a standard packaging practice of pharmaceutical companies, the pre-filling of unit dose injection cartridges has proven problematic. It is relatively easy to fill a cartridge if the cartridge is sealed at its distal end (e.g., nozzle face), inverted and left open at its proximal end. However, in order to seal the fluid chamber, a plug, cap or piston seal must then be forced into place, at the proximal end, against the sealed fluid. This can result in fluid spills and can slow a packaging line. Ideally, a unit dose injection cartridge would allow fluid medicament to be metered easily into the chamber, and then the chamber to be sealed, without requiring additional cumbersome steps for proper placement of the piston seal after filling of the chamber.

SUMMARY OF THE INVENTION

In view of the foregoing, it is a principal object of the present invention to provide a low cost unit dose injection cartridge (e.g., needleless injection cartridge) construction which permits a simplified method for filling the unit dose injection cartridges, with minimal or no medicament waste.

It is another object of the invention to provide a simplified injection cartridge filling method as aforesaid, which can be implemented as part of a mass production process for producing pre-filled unit dose injection cartridges, or as a filling step to be carried out at or about the time an injection is to be carried out.

These and other objects are achieved, in accordance with a first aspect of the present invention, by a unit dose injection cartridge. A sidewall structure defines an elongated medicament chamber of the cartridge. A sealable discharge outlet is provided at a distal end of medicament chamber. A discharge piston seal is slidable within the chamber from a proximal end region to a distal end region thereof The piston seal is removably securable at a first position within the proximal end region. A passageway extends, while the piston seal is in the first position, past the plunger from a proximal side to a distal side thereof The chamber is fillable with medicament by way of the passageway. During filling, air is allowed to escape from the chamber. The piston seal is movable distally to a second position within the proximal end region, after filling of the chamber, to thereby seal-off the chamber from the passageway.

In a second aspect, the invention is embodied in a method of filling a unit dose injection cartridge including an elongated chamber, a sealable discharge outlet at a distal end of the chamber and a piston seal slidable within the chamber from a proximal end region of the chamber to the distal end. The piston seal is removably secured at a first position within the proximal end region such that a passageway is formed extending past the plunger from a proximal side to a distal side thereof The chamber is filled with medicament through the passageway while simultaneously allowing air to escape from the chamber. Once a unit dose of medicament is metered into the chamber, the piston seal is moved distally to a second position within the proximal end region, to thereby seal-off the chamber from the passageway, while permitting any air remaining in the chamber to escape from the chamber.

In a third, more general aspect, the invention is embodied in a sealable or semi-sealed vessel. A sidewall structure defines an elongated chamber of the vessel. A sealable discharge outlet is provided at a distal end of the chamber. A discharge piston seal is sidable within the chamber from a proximal end region to a distal end region thereof. The piston seal is removably securable at a first position within the proximal end region. A passageway extends, while the piston seal is in the first position, past the plunger from a proximal side to a distal side thereof. The chamber is fillable with a liquid by way of the passageway. During filling, air is allowed to escape from the chamber. The piston seal is movable distally to a second position within the proximal end region, after filling of the chamber, to thereby seal-off the chamber from the passageway.

The above and other objects, features and advantages of the present invention will be readily apparent and fully understood from the following detailed description of preferred embodiments, taken in connection with the appended drawings.

BRIEF DESCRIPTION OF THE DRAWINGS

FIGS. 2A–2C are longitudinal cross-sectional views of an injection cartridge like the one shown in FIG. 1, illustrating sequential stages in accordance with the filling method of the invention.

FIG. 3 is a proximal end perspective view of an injection cartridge similar to those shown in FIGS. 1 and 1A–1C.

FIG. 4 is a side elevational view of an injection cartridge similar to the one shown in FIG. 3, but having a modified distal end (spacer) configuration.

FIG. 5 is a distal end elevational view of the injection cartridge shown in FIG. 4.

FIGS. 6 and 7 are cross-sectional views taken on lines B—B and E—E of FIG. 5, respectively.

DETAILED DESCRIPTION OF THE PREFERRED EMBODIMENTS

Figure 1:
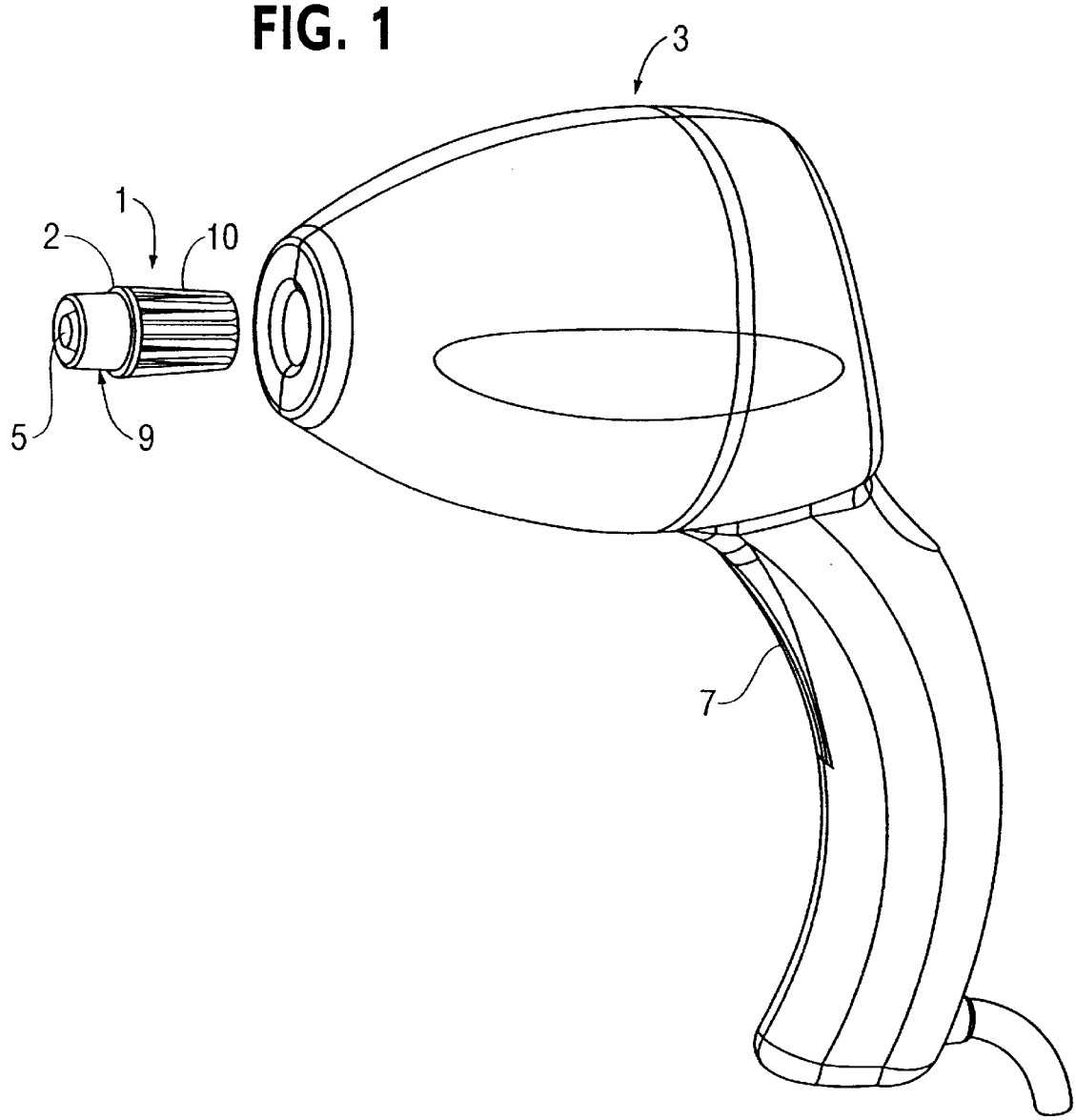
FIG. 1 is a perspective assembly view illustrating a needleless unit dose injection cartridge in accordance with the present invention, together with a depiction of an injector into which the cartridge is insertable for carrying out a needleless injection.
Figure 8:
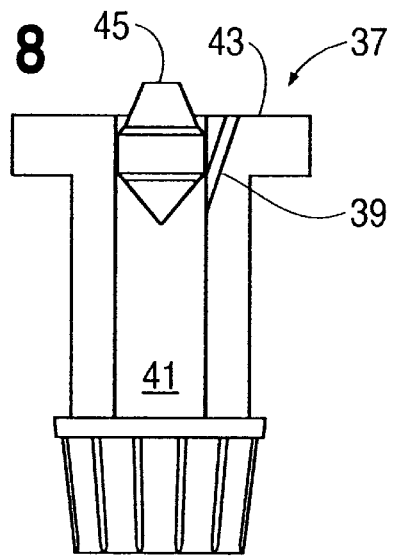
FIG. 8 is a side-elevational view, partially in section, showing an alternative injection cartridge embodiment of the present invention, with a piston seal thereof in a first, filling position.
Figure 9:
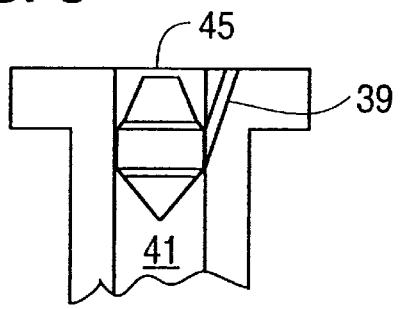
FIG. 9 is a close-up partial sectional view of the injection head shown in FIG. 8, showing the piston seal thereof advanced to a second, sealing position.
Figure 10:
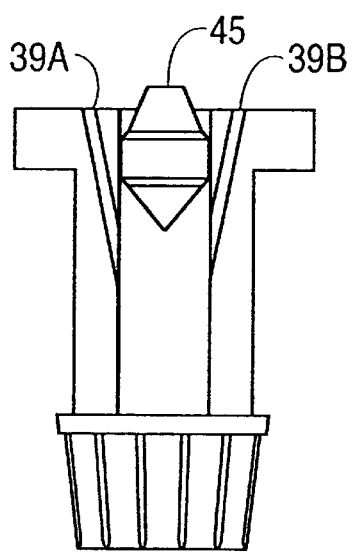
FIG. 10 is a side-elevational view, partially in section, of a further injection cartridge embodiment of the present invention.

Referring first to FIG. 1, a needleless unit dose injection cartridge 1 in accordance with the present invention is shown, together with an injector 3 into which cartridge 1 is insertable for carrying out a needleless injection. Injector 3 has a mechanism for advancing a piston seal of cartridge 1 through an injection stroke while cartridge 1 is held securely in place in the front end of the injector. This mechanism may be generally similar to that of the injector disclosed in commonly assigned U.S. Pat. No. 5,746,714. As disclosed in the '714 patent, the driving mechanism may comprise an air piston driven by a relatively low-pressure air source (not shown). The air piston drives the piston seal forward to force medicine in the chamber of cartridge 1 through an injection nozzle 5 located at the distal end of the chamber, to form a high pressure injection stream. Unlike the apparatus described in the '714 patent, cartridge 1 is preferably provided as a pre-filled unit dose injection cartridge, such that a provision on the injector for filling the cartridge (as described in the '714 patent) is unnecessary. Various means can be used for removably locking cartridge 1 in injector 3, such as a locking mechanism that grips cartridge 1 behind circumferential rim 2 by way of expandable jaws that close after cartridge 1 is inserted from the front. Alternatively, the cartridge and injector could be configured such that the cartridge is loaded into and locked in the injector from the rear, similar to a rifle breach. A further possibility is to utilize a ¼ turn bayonet lock with tabs, ball locks, gate locks, etc. FIGS. 8–10 show cartridge embodiments of the invention including at the proximal end a ¼ turn bayonet lock tab design for retention of the cartridge, similar to the locking tabs illustrated in copending application Ser. No. 08/819,563. Actuation of the air piston to drive the piston seal of cartridge 1 through an injection stroke may be initiated by a handle-mounted trigger button 7, or the like.

A chamber-forming wall structure 9 of cartridge 1 includes on its outside a ribbed portion 10 extending in a tapering fashion from an intermediate point along the length of the cartridge to the proximal end thereof This facilitates manual handling of the cartridge, and provides a gripping surface (rim 2) for locking the cartridge within injector 3.

As clearly seen in FIGS. 2A–2C, wall structure 9 defines, on its inside, an elongated chamber 11. A standard piston seal 13, e.g., utilizing O-rings and/or boots, is slidable within chamber 11 from a proximal end region 15 to a distal end 16 of the chamber. Piston seal 13 is movably securable at a first position within proximal end region 15, as shown in FIGS. 2A and 2B. With piston 13 in this position, a passageway 17 is formed, extending past piston seal 13 from a proximal side to a distal side thereof. Passageway 17 is provided between piston seal 13 and an adjacent laterally recessed chamber wall portion 19. Piston 13 should be sized such that its sealing fins are maintained in liquid-tight sealing contact with the interior chamber walls about the circumference of the chamber, except at the laterally recessed chamber wall portion 19 where passageway 17 is formed. Passageway 17 permits filling of chamber 11 with medicament by way of a vial or syringe 21, and attached cannula 23. Passageway 17 is preferably sized large enough to permit free insertion of cannula 23 therein, and air to escape from chamber 11 while the chamber is filled with medicament. Preferably, during the filling of chamber 11, cartridge 1 is oriented vertically. The flowing of medicament into chamber 17 may occur by force of gravity. Alternatively, the medicament may be injected into cartridge chamber 11 under pressure, e.g., by way of a manual syringe, or, especially in the case of pre-filling as part of a mass production process, by automated filling means.

A discharge nozzle 25 is formed at the distal end of the chamber, and includes an orifice 27. In order to avoid contamination, a removable seal 29 is preferably placed over the face of the nozzle (and orifice 27) during the filling operation. Seal 29 may take any suitable form, such as a thin plastic or foil layer lightly adhered about a rim of the nozzle face (Adhesive at the orifice should be avoided, in order to avoid occluding or contaminating the orifice.) Alternatively a cover could be provided in the form of a molded over-cap of plastic or metal.

Once a unit dose of medicament is metered into chamber 11, piston seal 13 may be moved slightly distally to a second position within proximal end region 15, as illustrated in FIG. 2C. Preferably, a very small circumferentially extending detent or step 18 (see FIG. 2C) is formed along the inside of wall structure 9 in order to precisely define the second position and provide a tactile indication of when the piston has reached the second position, by entry of a sealing fin of the piston into the detent. During this movement of the piston seal, and before the chamber is sealed-off, air remaining in the chamber is allowed to escape through passageway 17, thereby avoiding the need for leakage of medicament through nozzle orifice 27.

The foregoing filling steps typically will be performed as part of an automated process for mass producing pre-filled unit dose injection cartridges. Alternatively, empty cartridges could be provided to the user with piston seal 13 in the first position, and the filling procedure could be carried out manually by the user. In either case, after filling using a syringe or the like to inject medicament through passageway 17, an appropriate plunger stem-like tool could be used to advance the piston seal to the second position, to place cartridge 1 in condition for use. Proper displacement of the piston may be assured by controlling the stroke length of the stem-like tool, and/or by way of the tactile indication provided when a fin of the piston seal enters small detent 18. Also, generally a user will sense that the second position of the piston seal has been reached when substantially increased resistance to further forward movement of the piston seal is encountered, as a result of a fluid lock occurring once all air has escaped from the chamber and the passageway has been sealed.

FIG. 3 shows more clearly, in an injection cartridge 1' similar to cartridge 1 of preceding FIGS. 1–2C, a laterally recessed wall portion 19' forming a passageway to the side of a piston seal, when the piston seal is placed in the first position (as shown in FIGS. 2A, 2B). The precise shape and size of recessed wall portion 19' can be varied. Again, the recess preferably will create (with the piston seal) a passage large enough to allow insertion of a filling cannula, with sufficient space remaining about the cannula to allow air to escape from the chamber during filling. On the other hand, the recess should not be made so large as to significantly diminish the seal retention strength of the seal/chamber wall interface. In addition, preferably the passageway is small enough to resist leakage from the chamber even when open, e.g., under shaking or inversion. The distal end of recessed wall portion 19' has a taper region 31 to allow the piston to move smoothly into the second, sealing position. The piston seal and chamber bore should be sized and configured relative to each other such that once the seal is placed in the second, sealing position, the seal created by the piston seal is sufficiently strong to avoid "blow-by" of medicament during the high pressure injection stroke. Blow-by can be a problem if the piston seal is too soft, or does not mate well with the chamber. FIG. 3 also shows as part of the outer rib structure of the cartridge 1' a channel 33 within ribbed portion 10', serving to index a filling mechanism, e.g., cannula or nozzle, so that it lines up with the recessed wall portion 19' (and the passageway formed thereby).

FIGS. 4–7 show an injection cartridge 1' much like that shown in FIG. 3, but differing somewhat in external structure. Cartridge 1' has radially extending fin structures 35 at the distal end serving to provide a stable skin contact structure of increased effective diameter and/or less mass as compared to the continuous cylindrical structure surrounding the nozzle in the previous embodiments. The arrangement of fins also facilitates molding in that a closer ratio of wall thickness can be maintained throughout the part. All of the other elements of this embodiment correspond to the previous embodiments, and are correspondingly numbered.

With reference to FIGS. 8 and 9, a further embodiment of the invention is shown, in the form of a needleless injection cartridge 37 having a discrete passageway 39 formed in the sidewall of the cartridge, separate from a chamber 41 thereof. The passageway extends from a proximal end face 43 of the cartridge, and angles inwardly to a point of intersection with chamber 41. This outlet resides on a distal side of a piston seal 45, when piston seal 45 is placed in an initial filling position, as shown in FIG. 8. As shown in FIG. 9, piston seal 45 is advanceable to a second position wherein piston seal 45 serves to seal-off chamber 41 from the passageway. Similar to the previous embodiments, passageway 39 is preferably sized slightly larger than the filling cannula, to allow for air to escape from chamber 41 through passageway 39 during filling. On the other hand, passageway 39 is preferably sized small enough to resist leakage from chamber 41, e.g., under shaking or inversion, even when open, i.e., before piston seal 45 is moved to the second, sealing position.

In the alternative embodiment shown in FIG. 10, a pair of discrete passageways 39A, 39B, similar to passageway 39 of previous embodiment, are provided: one to allow for filling, and the other to allow air to escape from the chamber during the filling. As shown, passageways 39A, 39B can be configured similarly and arranged on opposite sides of the piston seal 45. A pair of passageways as shown in FIG. 10 could, instead of being formed as discrete passageways, be provided in the form of a pair of laterally recessed wall portions similar to the embodiments of FIGS. 1–7. A potential drawback of a two passageway embodiment is that, until the piston seal is moved to the second sealing position, leakage may occur through passageways 39A, 39B, by virtue of the loss of an air-lock effect.

The described injection cartridges of the present invention can be formed in various known ways, using various known materials, including metals and plastics. Preferably, the cartridges are formed by injection molding of thermoplastic resin, as taught in co-pending U.S. application Ser. No. 08/819,563. Suitable thermoplastic resins include, but are not limited to styrenic blends (e.g., K-resin), polyethylene teraphalate (e.g., PET-G), polycarbonate and medical grade silicone. The cartridge could also be made of stamped or formed metal. The discrete passageways of the embodiments of FIGS. 8–10 can be formed as part of the injection molding of the cartridges, or formed after molding by drilling or the like. The laterally recessed chamber wall portions of the other embodiments (FIGS. 1–7) likewise can be formed as part of the cartridge molding process, or in a post-molding machining step.

While the preferred embodiments described herein comprise needleless unit dose injection cartridges, the invention is not so limited. The invention may be applied with similar advantages to unit dose injection cartridges, or ampules, used with conventional hypodermic needle cannula syringes and the like.

The present invention has been described in terms of preferred and exemplary embodiments thereof Numerous other embodiments, modifications and variations within the scope and spirit of the appended claims will occur to persons of ordinary skill in the art from a review of this disclosure.

What is claimed is:

1. A unit dose injection cartridge comprising:
 a sidewall structure defining an elongated medicament chamber;
 a sealable discharge outlet at a distal end of said medicament chamber;
 a discharge piston seal slidable within the chamber from a proximal end region to a distal end region thereof, said piston seal being removably securable at a first position within the proximal end region;
 a passageway extending, while said piston seal is in said first position, past the plunger from a proximal side to a distal side thereof, the chamber being fillable with medicament by way of the passageway, wherein:
 during filling, air is allowed to escape from the chamber; and
 the piston seal is movable distally to a second position within the proximal end region, after filling of the chamber, to thereby seal-off the chamber from the passageway.

2. A unit dose injection cartridge according to claim 1, further comprising a discharge outlet seal, wherein when said piston seal is in said first position and said discharge outlet seal is intact, said chamber is sealed except for said passageway, which permits the escape of air from the chamber during said filling.

3. A unit dose injection cartridge according to claim 1, further comprising a discharge outlet seal and a second passageway extending, while said piston seal is in said first position, past the plunger from the proximal side to the distal side thereof, wherein when said piston seal is in said first position and said discharge outlet seal is intact, said chamber is sealed except for said first and second passageways, said second passageway permitting the escape of air from the chamber during said filling through the first passageway.

4. A unit dose injection cartridge according to claim 3, wherein said first and second passageways are formed as discrete passageways extending through said sidewall structure of the cartridge.

5. A unit dose injection cartridge according to claim 1, wherein the passageway is provided between the piston seal and an adjacent laterally recessed chamber wall portion.

6. A unit dose injection cartridge according to claim 1, wherein the passageway is formed as a discrete passageway extending through said sidewall structure of the cartridge.

7. A unit dose injection cartridge according to claim 1, wherein said cartridge is a needleless injection cartridge, and said discharge outlet is a discharge nozzle orifice.

8. A unit dose injection cartridge according to claim 7, further comprising a removable seal covering said nozzle orifice.

9. A method of filling a unit dose injection cartridge including an elongated chamber, a sealable discharge outlet at a distal end of the chamber and a piston seal slidable within the chamber from a proximal end region of said chamber to said distal end, said method comprising:
 removably securing the piston seal at a first position within the proximal end region such that a passageway extending past the plunger from a proximal side to a distal side thereof is formed;
 filling said chamber with medicament through said passageway while simultaneously allowing air to escape from the chamber;
 once a unit dose of medicament is metered into the chamber, moving the piston seal distally to a second position within the proximal end region, to thereby seal-off the chamber from the passageway while permitting any air remaining in the chamber to escape from the chamber.

10. A method according to claim 9, wherein said chamber is, but for a communication with atmosphere provided by said passageway, maintained in a sealed condition during said chamber filling step.

11. A method according to claim 4, wherein said escape of air during filling occurs through a second passageway which extends past the plunger from a proximal side to a distal side thereof, when said piston seal is in said first position.

12. A method according to claim 4, wherein said filling step is carried out by inserting a cannula into said passageway and flowing said medicament into said chamber through said cannula.

13. A method according to claim 6, wherein said cartridge is oriented vertically during said filling step, and said flowing of medicament into the chamber occurs by force of gravity.

14. A sealable or semi-sealed vessel comprising:

a sidewall structure defining an elongated chamber, a sealable discharge outlet at a distal end of said chamber;

a discharge piston seal slidable within the chamber from a proximal end region to a distal end region thereof, said piston seal being removably securable at a first position within the proximal end region;

a passageway extending, while said piston seal is in said first position, past the plunger from a proximal side to a distal side thereof, the chamber being fillable with a liquid by way of the passageway, wherein:

during filling, air is allowed to escape from the chamber; and the piston seal is movable distally to a second position within the proximal end region, after filling of the chamber, to thereby seal-off the chamber from the passageway.

\* \* \* \* \*